United States Patent [19]
Moulding

[11] 3,933,152
[45] Jan. 20, 1976

[54] INTRAUTERINE CONTRACEPTIVE DEVICE

[76] Inventor: Thomas S. Moulding, 1954 Glencoe, Denver, Colo. 80220

[22] Filed: Feb. 19, 1974

[21] Appl. No.: 443,338

Related U.S. Application Data

[63] Continuation-in-part of Ser. No. 189,212, Oct. 14, 1971, Pat. No. 3,802,425.

[52] U.S. Cl. .............................. 128/129; 128/130
[51] Int. Cl.² .......................................... A61F 5/46
[58] Field of Search ........... 128/127, 128, 129, 130, 128/172, 260

[56] References Cited
UNITED STATES PATENTS

| | | | |
|---|---|---|---|
| 3,401,689 | 9/1968 | Greenwood | 128/129 |
| 3,405,711 | 10/1968 | Bakunin | 128/130 |
| 3,452,749 | 7/1969 | Riedell | 128/129 |
| 3,464,409 | 9/1969 | Murphy | 128/129 |
| 3,515,132 | 6/1970 | McKnight | 128/130 |
| 3,658,057 | 4/1972 | Cimber | 128/129 |
| 3,786,808 | 1/1974 | Lerner | 128/130 |
| 3,820,535 | 6/1974 | Marco | 128/130 |
| 3,848,590 | 11/1974 | Kitrilakis | 128/129 |

FOREIGN PATENTS OR APPLICATIONS

| | | | |
|---|---|---|---|
| 981,389 | 1/1965 | United Kingdom | 128/130 |

*Primary Examiner*—Lawrence W. Trapp
*Attorney, Agent, or Firm*—Sheridan, Ross & Fields

[57] ABSTRACT

An intrauterine contraceptive device is provided which is inserted into a uterus in a collapsed position and is held in an expanded position by introduction of a self-hardening liquid plastic into the device after it is positioned within the uterus. In one embodiment the device is provided with an inflatable membrane for positioning it within the uterus prior to insertion of the liquid plastic, after which the membrane is deflated and in some instances removed. In another embodiment the device comprises a plastic tube with a resilient rod therein which may be deformed to insert the device in the uterus and after being positioned therein a liquid self-hardening plastic is introduced into the tube to hold the resilient rod in an expanded position that conforms to the uterine cavity. In still another embodiment, the rod is arranged to telescope in a tubular member which tubular member can be filled with self-hardening liquid plastic to force the rod out of the end of the tubular member and against a wall of the uterus and to hold it permanently in that position. In addition a tubular member may be provided an angular connection thereof which can be filled with the self-hardening liquid plastic to form a more rigid structure after the device is positioned in the uterus. If desired, a resistance heating element can be provided within the device to melt or soften the plastic so that the device can be removed from the uterus at a later time.

12 Claims, 13 Drawing Figures

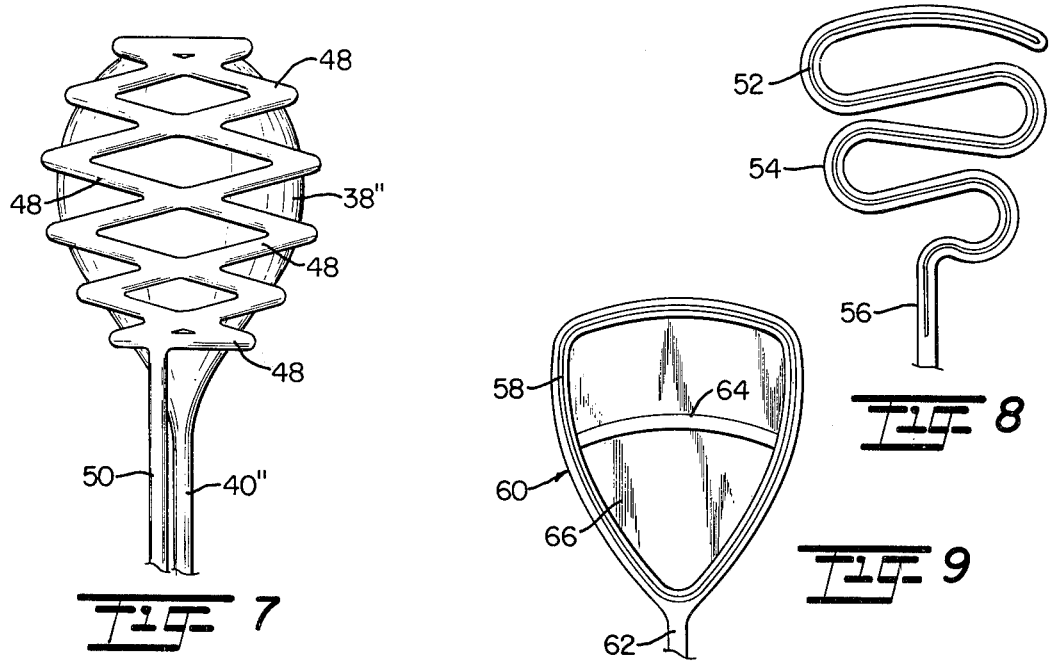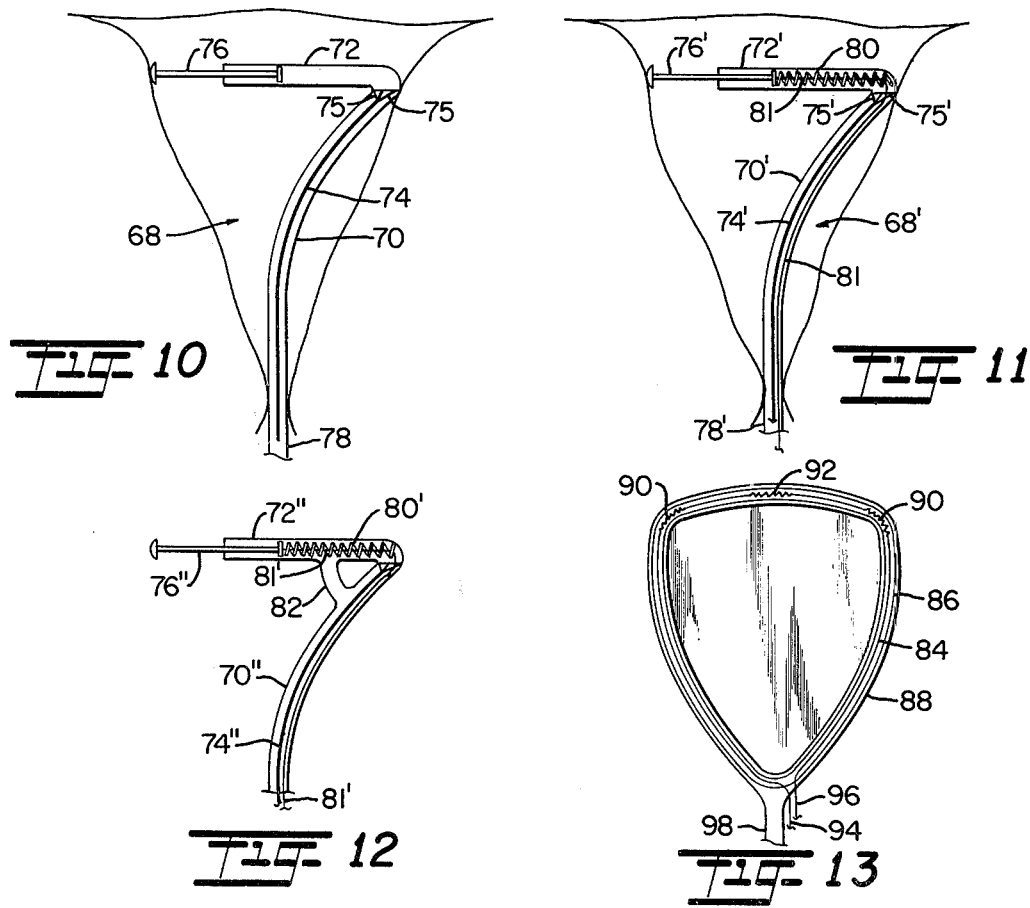

INTRAUTERINE CONTRACEPTIVE DEVICE

This application is a continuation-in-part application of my copending application Ser. No. 189,212, filed Oct. 14, 1971 which issued on Apr. 9, 1974 as U.S. Pat. No. 3,802,425.

BACKGROUND OF THE INVENTION

1. Field of the Invention

This invention relates to an intrauterine contraceptive device, and more particularly to such a device wherein a liquid plastic material is introduced into the device after it is positioned in the uterus and hardens therein to make the device substantially rigid.

DESCRIPTION OF THE PRIOR ART

As the effects of increased population become increasingly severe, resulting in environmental conditions which are deteriorating at an alarming rate, more and more effort is being placed on means for slowing the increase in world population, if not entirely halting such increase.

One type of contraception which has found considerable acceptance is the intrauterine contraceptive device, commonly known as an IUD. The IUD is a device which is placed inside the uterus, a soft tissue organ made primarily of smooth muscle. The way in which it operates to prevent pregnancy is not entirely understood but it is well known that any foreign body placed in the uterus has a contraceptive effect which is 90 to 95% effective. However, some such devices which have been used have caused the walls of the uterus to become eroded or partially penetrated causing pain and bleeding to the user, thereby necessitating removal. In many instances the IUDs are expelled from the uterus and this is believed to be because they are generally too small or not sufficiently rigid. However, when larger IUDs are used, there is a greater instance of pain and bleeding and sometimes the IUD induces contractions of the uterus which may lead to expulsion.

IUDs have been constructed in numerous shapes and sizes and of various materials, but each has had certain deficiencies. One IUD was made by injecting silastic into the uterus which then set up to form a cast. However, this procedure was abandoned because of the high incidence of expulsions, probably due to the distention of the uterus in the anterior-posterior diameter. A popular form of IUD is the Lippes Loop which is a sinusoidal spring-like device which is stretched into a linear shape and inserted into the uterus after which it contracts to fill the uterine cavity, but lies only in one plane namely the plane of the uterine cavity and does not significantly expand the cavity in the anterior-posterior diameter. However, with resilient devices the chance of expulsion is greater than with more rigid devices.

SUMMARY OF THE INVENTION

In accordance with the present invention the principle of casting is used in order to properly fit the IUD to the uterus and substantially fill it in the plane thereof. Such a device has a minimum anterior-posterior thickness to minimize the possibility of inducing contractions of the uterus and has sufficient rigidity to minimize the possibility that the device will be expelled from the uterus. Such a device comprises a member insertable into the uterus in a collapsed position and movable into an expanded or extended position within the uterus and further includes an initially collapsed means for receiving a self-hardening liquid plastic either before or after the IUD is positioned in the uterus of a quantity sufficient to hold the member in the expanded position after hardening to form a cast. In other words, these members have at least one potential cavity which can be inflated with the self-hardening liquid plastic. Conveniently, by having the self-hardening plastic in a member within the uterine cavity, rather than in the uterine cavity without a covering, liquid plastic materials can be used which would not otherwise be suitable for use in a body cavity. In addition, the device will conform to the shape of a uterus which may be deformed by the presence of fibroids therein.

More particulaly, the invention comprises in one embodiment an inflatable membrane surrounded by a collapsible tubular plastic channel. The device is inserted, as by an insertion tube, into the uterus after which the membrane is filled with carbon dioxide to expand the device to substantially fill the uterine cavity and then while in an expanded position, the collapsed tubular member is filled with a self-hardening liquid plastic to expand it. After the plastic hardens to form a cast the inflatable member can be deflated and, if desired, removed from the uterus. The tubular member may taken any one of several forms, that is, it may extend along the longitudinal dimensions of the inflatable member or it may be wound therearound in a helix configuration or may consist of a series of tubular members extending from one end of the inflatable member to the other which tubular members are interconnected. In a further embodiment these tubular members may have a mesh configuration.

In a still further embodiment the device may comprise a sinusoidal shaped resilient plastic rod in the form of a Lippes Loop surrounded by a tubular plastic member which may be filled with self-hardening liquid plastic after the IUD is inserted in the uterus to minimize expulsion. In still another form of the invention a closed plastic loop may be provided which is surrounded by a tubular member which may be filled with self-hardening liquid plastic after the IUD is introduced into the uterus to form a cast. In this embodiment a membrane may extend across the closed loop.

A still further embodiment may be comprised of a rod which is extensible from one end of a tube which has a resilient rod attached at an angle thereto to form a device in the shape of the number seven. A collapsible tube extends over the depending rod and is in communication with the other tube. The legs of the seven are bent together and inserted in the uterus whereupon one leg snaps back to a position in which it extends generally across the uterus. A liquid plastic material is inserted into the collapsed tube which forms the depending leg of the IUD to force the rod in the other leg outwardly against the opposite wall of the uterus whereupon the liquid plastic hardens to hold the rod in position. A modification of this IUD can include a spring member that can be released after the seven is positioned in the uterus for urging the rod outwardly. The liquid plastic surrounds the spring and upon hardening holds the spring so that it will not further force the rod into the wall of the uterus thereby minimizing the chance of eroding the uterine wall or penetrating the same. Furthermore, a tubular member, which is fillable with a self-hardening liquid plastic, can be provided across an angle thereof to create a more rigid angle after the device is positioned in the uterus.

If desired, a resistance heating element may be included in the device which has connections extending into the inferior portion of the uterine cavity when the IUD is in place. If it is necessary at a later time to remove the IUD a source of electric current can be attached to these connection so that the resistance heating element melts or softens the plastic material forming the cast to permit withdrawal of the IUD.

Additional advantages of this invention will become readily apparent from the description which follows, taken in conjunction with the accompanying drawings.

BRIEF DESCRIPTION OF THE DRAWINGS

FIG. 7 is a front elevation similar to FIGS. 5 and 6 showing a further modification wherein the tubular member is in a meshed configuration surrounding an inflatable member;

FIG. 8 is a front elevation of an intrauterine device of this invention which is in the form of a Lipper Loop within a tubular member;

FIG. 9 is a front elevation of a further modification of the invention wherein a closed loop is provided within a tubular member having a membrane thereacross;

FIG. 10 is a front elevation of an IUD in the shape of the numeral seven when positioned within a uterus as shown;

FIG. 11 is an elevation, similar to FIG. 10, but showing an IUD having a spring for urging the rod toward the uterine wall;

FIG. 12 is a front elevation, similar to FIGS. 10 and 11, but showing a tubular portion interconnecting the two legs of the IUD for receiving self-hardening plastic material; and FIG. 13 is a front elevation, similar to FIG. 9, but showing a resistance heating element within the rod to facilitate removal of the IUD.

DESCRIPTION OF THE PREFERRED EMBODIMENTS

In accordance with this invention a form is introduced into the uterus which form is made of plastic sheets or tubes, such as polyethylene, with barium imbedded therein to make them opaque to X-ray radiation which are biomedically compatible with the uterus and are used to make a cast which forms an IUD with minimal anterior-posterior thickness. After the form is introduced into the uterine cavity it is aligned in the plane of the uterine cavity and then filled with a liquid plastic that will harden quickly. An example of suitable material is a monomer such as methyl methacrylate and a free radical catalyst such as benzoyl peroxide or methyl ethyl ketone peroxide or hydrogen peroxide. Alternatively, the plastic material could be made of styrene monomer or unsaturated polyester resins plus one of the free radical catalysts referred to above. Many other combinations of resins and catalysts can be used for polymerization or crosslinking to make the self-hardening plastic. The plastic form consists of collapsible tubes, preferably on the order of 1½ mm. in diameter which are connected to sheets of polyethylene, as will be more fully described below.

If desired, the free radical catalyst can be placed in the tubes prior to insertion of the IUD into the uterine cavity. This eliminates the necessity of mixing the liquid with the catalyst prior to injection and still allows the liquid to harden after it is injected into the tubes so that it will harden in the uterus. To avoid the possibility that the hardening will occur before the plastic has entirely filled the tubes, the free radical catalyst can be placed in the portions of the tube or tubes that the plastic reaches last when injected. A slow hardening plastic can even be placed in the tube or tubes prior to insertion. The tubes may have many different arrangements as described before but a principle which is important is that the plastic form which is used to make a cast that fits the uterus does not have excessive thickness.

Figure 1:
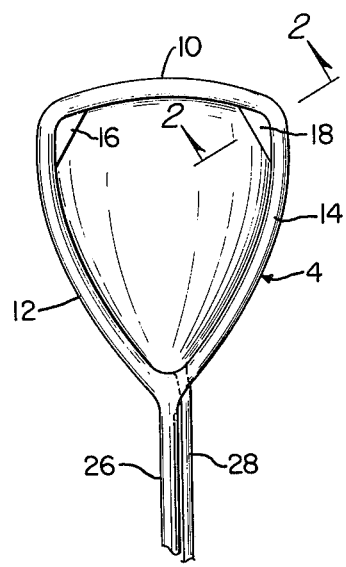
FIG. 1 is a front elevation of one form of IUD comprising the invention.
Figure 2:
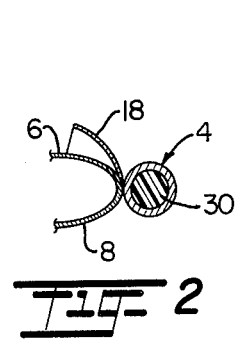
FIG. 2 is an enlarged section, taken along line 2—2 of FIG. 1, showing further details of the construction of the IUD of FIG. 1.
Figure 3:
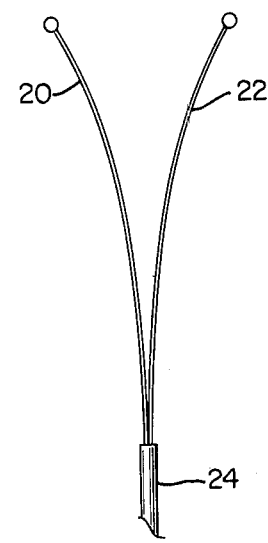
FIG. 3 is a fragmentary elevation of a sound for use within an insertion tube for inserting the IUD into a uterus.

An IUD is disclosed in FIG. 1 which comprises a tubular loop 4 having the general shape of a uterus in the plane thereof, the loop being covered by a pair of spaced membranes 6 and 8, as best seen in FIG. 2, which form an enclosed area which is adapted to be filled with air, as described more fully below. These membranes 6 and 8, in effect, form a balloon to which the tubular member or loop 4 is attached. The tube comprises a leg 10 which is positioned in the fundus of the uterus. Leg 10 has two depending legs 12 and 14 which are joined at an angle at the end which is adjacent the cervix when the IUD is in position. The IUD is provided with a pair of pockets 16 and 18 respectively, which are at the cornual portions of the device at the juncture of legs 10 and 12 and 10 and 14, respectively. These pockets are adapted to receive the distal ends of tines 20 and 22 respectively, of sound 24 for insertion of the device into the uterus. The tines are made of a resilient material and normally assume the spaced positioned shown in FIG. 3.

The IUD is placed in an insertion tube (not shown) of conventional structure which is of a diameter of 3 mm. or less with tines 20 and 22 in pockets 16 and 18. The insertion tube together with the IUD and sound 24 is inserted into the uterus until it engages the fundus at which time the insertion tube is withdrawn which allows the tines to spring apart as in FIG. 3 to position the corners formed by the juncture of leg 10 and with legs 12 and 14, respectively, of tubular member 4 in the cornua of the uterus. Tubular member 4 is provided with an inlet tube 26 which extends out through the cervix and a similar inlet tube 28 is provided which communicates with the space between membranes 6 and 8. After the IUD is positioned in the uterus and the sound removed, air is introduced between membranes 6 and 8 by means of tube 28 to inflate the device and hold it in the proper position within the uterus. While still inflated, the liquid plastic material is introduced through inlet 26 into loop 4 which is filled with the plastic which plastic will become hard and rigid to form a plastic ring or form 30 as shown in FIG. 2. After the plastic has hardened, tube 28 can be opened to let the air out from between membranes 6 and 8. Finally, the end of inlet 26 can be clipped off by a suitable surgical tool adjacent loop 4.

Figure 4:
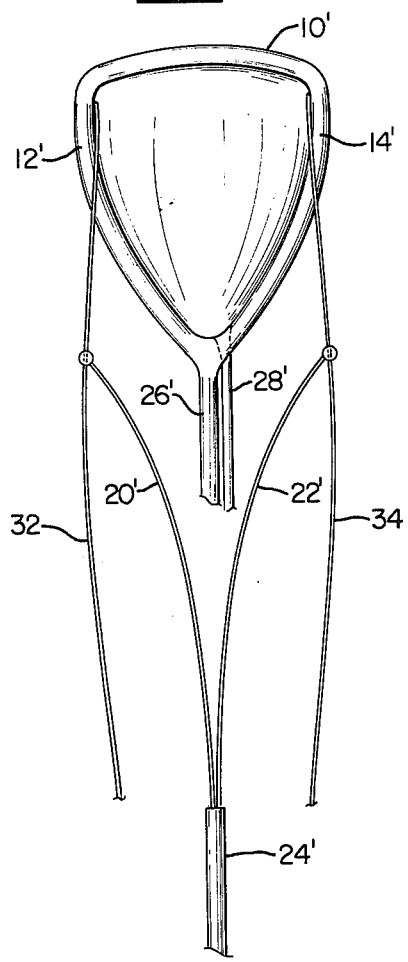
FIG. 4 is a front elevation showing a further embodiment of an IUD having threads attached thereto for use with a different sound for insertion of the IUD in a uterus.

An alternative method of inserting the IUD in the uterus is disclosed in FIG. 4 wherein pockets 16 and 18 are replaced with threads 32 and 34 connected adjacent the leading end of the IUD as shown and is used in conjunction with a sound 24' wherein the distal ends of tines 20' and 22' are provided with apertures for receiving the ends of threads 32 and 34. With this enbodiment, by maintaining tension on threads 32 and 34, the IUD, which is positioned in an insertion tube, can be pushed into the uterus by means of sound 24' into engagement with the fundus of the uterus. Once positioned, the sound 24' can be withdrawn and the tines will spring into the cornua of the uterus and the device is inflated through inlet tube 28 and filled with liquid self-hardening plastic material through inlet tube 26', as described above with respect to FIG. 1.

Furthermore, a method of inserting an IUD is contemplated which does not require an insertion tube. In this method a single thread is attached to an end of an IUD to be positioned against the fundus which thread is placed through an aperture in a single tine of a sound. The IUD is inserted by means of the sound while the thread is held taut. The thread is then released and the sound withdrawn. Advantageously, this method minimizes distension of the cervix and hence reduces any pain associated with the insertion of an IUD.

Figure 5:
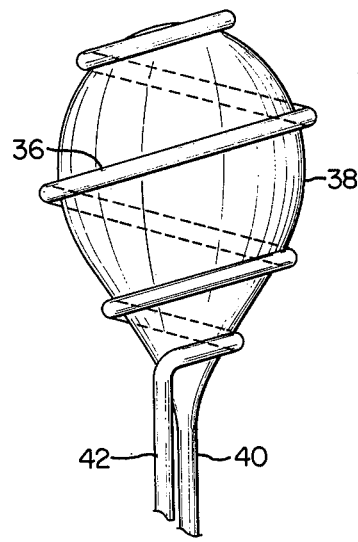
FIG. 5 is a front elevation of a further alternative embodiment wherein a tubular member is wrapped in helical configuration about an inflatable member.

An alternative embodiment shown in FIG. 5 wherein a tubular member 36 is wound in a helical configuration around a balloon 38, and is attached thereto. The device when uninflated may be placed in an insertion tube, with a single tine sound (not shown) within the balloon, and inserted in the uterus after which insertion tube is withdrawn, then the sound is withdrawn and the balloon 38 inflated through an inlet tube 40 extending out through the cervix. After the balloon has been inflated liquid plastic can be inserted in the tubular member 36 through inlet 42. After the liquid plastic hardens, balloon 38 can be deflated. The balloon can be detachably attached to tubular member 36, as by perforations, so that it can be withdrawn through the cervix rather than remaining in the uterus.

Figure 6:
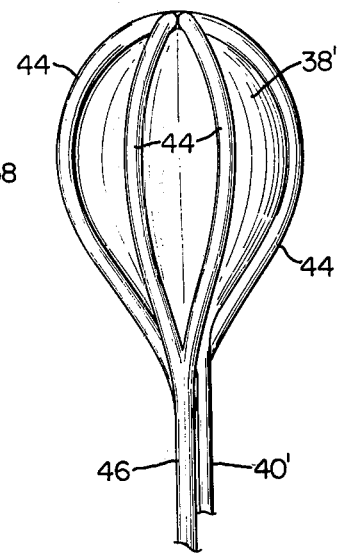
FIG. 6 is a front elevation similar to FIG. 5 of a further modified embodiment wherein the tubular members extend longitudinally from one end of an inflatable member to the opposite end and are interconnected.

A further embodiment is shown in FIG. 6 wherein longitudinally extending tubular members 44 extend londitudinally of balloon 38' and are interconnected at the fundus and are connected to an inlet 46 so that the tubes may be filled with liquid plastic after the balloon 38' is inflated through inlet 40'.

A further embodiment is shown in FIG. 7 wherein balloon 38'' is covered by a mesh network of tubular members 48 all interconnected with each other and connected to an inlet 50 through which liquid plastic may be introduced after bag 38' is inflated through tube 40''.

An alternative embodiment is shown in FIG. 8 wherein the sinusoidal rod 52, such as polyethylene is in the form of a Lippes Loop and is positioned within a similarly shaped polyethylene tubular member 54. This composite structure may be placed in the uterus by means of an insertion tube in a method well known to those skilled in the art after which a self-hardening liquid plastic, of the type previously described, can be introduced through an inlet 56 which extends into the cervix. Advantageously, the rod 52 is resilient for insertion and has less rigidity than the Lippes Loop so it can adapt to the uterine cavity size but after it is positioned in the uterus and the tube 54 filled with the liquid plastic which hardens the device becomes rigid and therefor cannot easily be expelled.

A still further embodiment is shown in FIG. 9 wherein a plastic resilient rod 58 is provided in the form of a closed loop which is made within a similarly formed tubular member 60 which has a depending inlet 62. Before insertion into the uterus the device may be compressed so as to fit within an insertion tube is placed in the uterus whereupon plastic rod 58 springs to its open extended position as shown in FIG. 9. Afterwards self-hardening liquid plastic material is introduced through inlet 62 whereupon the device becomes rigid so that it is not easily expelled by the uterus. In addition, a cross tube 64 may be provided for interconnecting the depending legs of loop 60 which tube is also filled with liquid plastic material to impart further rigidity to the structure. In addition, the loop may be covered by a plastic membrane 66 which minimizes the possibility that a portion of the bowel will protrude through the loop resulting in possible strangulation thereof if the IUD completely penetrates the uterine wall.

Another embodiment shown in FIG. 10 wherein the IUD 68 comprises a tubular member in the shape of the numeral seven, having a depending collapsible tubular leg 70 connected to a laterally extending leg 72 at the corner of the seven. To facilitate insertion, a resilient plastic rod 74 extends through collapsible leg 70 and is joined to leg 72 at the corner, as by a plurality of fingers 75 which have spaces therebetween for the passage of self-hardening liquid plastic as described below. Laterally extending leg 72 is hollow and is adapted to receive a rod 76. The device is placed in the uterus with the legs being bent together within an insertion tube and with leg 70 collapsed around rod 74. As the insertion tube is withdrawn leg 72 snaps open to the extended position shown in FIG. 10 due to the resilience of the corner. A self-hardening liquid plastic material is inserted through inlet 78 of depending collapsed leg 70, which leg extends into the cervix. The liquid plastic material passes between fingers 75 and pushes rod 76 out of extending leg 72 until it contacts the opposite wall of the uterus and then hardens in the tube to effectively lock rod 76 in position to minimize the possibility of expulsion.

An alternative embodiment shown in FIG. 11 wherein a spring 80 is provided with extending leg 72' of IUD 68'. The device is inserted as described above with respect to FIG. 10, but in this embodiment spring 80 urges rod 76' against the wall of the uterus. Conveniently a string or thread 81 is attached to the inner end of rod 76' and extends through spring 80 through fingers 75' and through collapsed tube 70' along side of resilient rod 74'. During insertion, thread 81 is pulled tight to hold spring 80 in a contracted position and to hold rod 76' within leg 72'. After insertion, the thread is released so that rod 76' is pushed by spring 80 against the uterine wall, as shown. The liquid plastic material is then inserted through inlet 78' to fill collapsed tube 70'. This material passes through fingers 75' and surrounds spring 80 where it hardens and holds the spring in a fixed position so that the tendency of rod 76' to be further urged into the uterine wall, thereby causing erosion or penetration thereof is substantially reduced.

A further alternative shown in FIG. 12 wherein IUD 68'' includes a tubular portion 82 interconnecting leg 70'' with leg 72''. As in the embodiment of FIG. 11, during insertion rod 76'' is held within leg 72' by pulling tight on thread 81' to contract spring 80' after which the tension is released and spring 80' pushes rod 76' against the uterine wall. Advantageously, tubular portion 82 then is filled with the self-hardening liquid plastic material as will the other tubular members thereby causing the corner to be more rigid thereby minimizing the chance of expulsion.

A problem that is encountered with the use of a rigid or semi-rigid IUD is removal of the device from the uterus at some later time. Obviously, if it is too rigid, it will be difficult to remove. To overcome this problem, a heating element can be included within the IUD as shown in FIG. 13 wherein a loop of electrical wire 84 is provided within resilient plastic rod 86 which in turn is within a tubular member 88. The wire 84 is provided with resistance heating elements 90 at the cornua and if desired, another heating element 92 in the leg of the IUD which is positioned against the fundus. Opposite ends of wire 84 extend through the device adjacent the cervical end to provide a pair of contacts 94 and 96. The device is inserted in the uterus in the same manner as the device of FIG. 9 and liquid plastic introduced into tubular member 88 through inlet 98 which extends into the cervix. At a later time if it is desired to remove the IUD a source of electric current is brought into engagement with contacts 94 and 96 to heat elements 90 and 92 so that rod 86 and the plastic material within tube 88 becomes soft and pliable to facilitate withdrawal of the IUD from the uterus. It will be apparent to one skilled in the art that an electrical circuit can be provided for use in any of the other IUDs disclosed herein. For example, in the IUD disclosed in FIG. 8, a wire could be run through rod 52 which comprises a Lippes Loop and bent back over itself at the end and run back through the rod so that both ends of the wire extend out of the device adjacent the cervical end of the uterus.

From the foregoing, the advantages of this invention are readily apparent. A device has been provided which is flexible and compact for easy insertion into the uterus but which can be expanded and positioned within the uterus to make a rigid form by use of a self-hardening liquid plastic material which is received in a tubular member comprising a portion of the IUD. Such a device is substantially rigid and substantially fills the uterus in the plane thereof to minimize the possibility of expulsion due to size but is of minimal thickness in the anterior-posterior direction and conforms to the uterine size in lateral directions to minimize the possibility of inducing contractions of the uterus. It also is made in such a fashion as to substantially reduce the possibility of erosion or partial penetration of the uterine wall. It will also conform to the configuration of the uterine cavity when the cavity is distorted from its usual shape, such as when there are fibroids in the uterus. In addition, if desired, a heating element may be provided within the device for softening the plastic material at a later date so that the device may be removed from the uterus.

The invention has been described in detail with particular reference to preferred embodiments thereof, but it will be understood that variations and modifications can be effected within the spirit and scope of the invention.

What is claimed is:

1. An intrauterine contraceptive device made of biomedical material and which conforms to the size and shape of the uterus after insertion therein, said device comprising:
    an inflatable member having a first inlet insertable into a uterus in a collapsed position and movable into an expanded position within the uterus upon introduction of a fluid into said member through said first inlet; and
    tubular means connected to and extending around the periphery of said inflatable member and having a second inlet for receiving a self-hardening liquid plastic so that after said device is positioned in the uterus and said inflatable member is expanded to position said tubular means against the uterine walls, the liquid plastic which has been introduced into said tubular means through said second inlet in said tubular means will hold said tubular means in position against the uterine walls after which said member is deflated.

2. An intrauterine contraceptive device as claimed in claim 1, wherein said inflatable member includes:
    a pair of peripherally sealed membranes which are inflatable for moving said member from said collapsed position to said expanded position to properly position said tubular means, said tubular means being connected to said membranes adjacent the peripheral seal thereof.

3. An intrauterine contraceptive device made of biomedical material and which conforms to the size and shape of the uterus after insertion therein, said device comprising:
    a pair of peripherally sealed membranes which are inflatable and have a broader portion with a substantially flat end and a narrower portion with a narrow end having the general shape and size of a uterus when inflated and including an inlet adjacent said narrower portion for filling the space between said membranes with a gas under pressure after said device has been placed in the uterus; and
    a tubular member extending around at least a portion of said membranes and having an inlet adjacent said inlet for receiving a liquid material to position said tubular member against the walls of the uterus and hold it in this position as a substantially rigid member after said membranes are deflated.

4. An intrauterine contraception device as claimed in claim 3, wherein said liquid material comprises:
    a self-hardening liquid plastic which hardens after being placed in said tubular member.

5. An intrauterine contraceptive device as claimed in claim 3, further including:
    means for inserting said device in a uterus.

6. An intrauterine contraceptive device as claimed in claim 5, wherein said inserting means includes:
    at least one pocket in the broader portion of said membrane for receiving a sound for inserting said device.

7. An intrauterine contraceptive device as claimed in claim 5, wherein said inserting means includes at least one thread attached to said broader portion of said membrane for receiving a sound with an aperture in the end thereof through which said thread extends during insertion of said device in a uterus.

8. An intrauterine contraceptive device as claimed in claim 3, wherein said tubular member comprises:

a single closed loop extending from said narrow end around said flat end and having said inlet depending from said narrow end.

9. An intrauterine contraceptive device as claimed in claim 3, wherein said tubular member comprises:
a helix extending around said membrane from said narrow end to said flat end and having said inlet extending from said narrow end.

10. An intrauterine contraceptive device as claimed in claim 3, wherein said tubular member comprises:
a plurality of tubes extending longitudinally along said membrane from said narrow end to said broad end, being interconnected with each other at both ends and having said inlet extending from each of said tubes at said narrow end.

11. An intrauterine contraceptive device as claimed in claim 3, wherein said tubular member comprises:
a net of tubes covering a substantial portion of the surface of said membrane, all of said tubes being interconnected and having an inlet extending from said narrow end.

12. An intrauterine contraceptive device as claimed in claim 3, further including:
a thread connected to a portion of said membranes which is engageable with the fundus when said membranes are positioned within said cavity, said device being positionable within the uterus by passing said thread through an opening in the end of a tine of a sound and pushing said device into the uterus.

* * * * *